United States Patent [19]

Hasson

[11] Patent Number: 5,217,466
[45] Date of Patent: Jun. 8, 1993

[54] GUIDE FOR FACILITATING THE PERFORMANCE OF INTERNAL SURGERY

[76] Inventor: Harrith M. Hasson, 2043 N. Sedgewick, Chicago, Ill. 60614

[21] Appl. No.: 688,114

[22] Filed: Apr. 19, 1991

[51] Int. Cl.[5] .................. A61B 17/00; A61B 19/00
[52] U.S. Cl. ..................... 606/119; 606/1; 606/108; 604/27; 604/55; 604/281
[58] Field of Search .............. 606/1, 96, 97, 98, 102, 606/119, 135, 108; 604/95, 27, 264, 281, 164, 55, 256; 128/778

[56] References Cited

U.S. PATENT DOCUMENTS

| | | | |
|---|---|---|---|
| 735,400 | 8/1903 | McCully | 606/119 |
| 2,905,178 | 9/1959 | Hilzinger, III | 606/1 |
| 3,796,211 | 3/1974 | Kohl | 604/281 |
| 3,805,767 | 4/1974 | Erb | 606/135 |
| 3,877,433 | 4/1975 | Librach | 606/119 |
| 4,000,743 | 1/1977 | Weaver | 606/119 |
| 4,022,208 | 5/1977 | Valtcher | 606/119 |
| 4,781,704 | 11/1988 | Potter | 604/281 |
| 4,935,017 | 6/1990 | Sylvanowicz | 604/281 |
| 4,960,411 | 10/1990 | Buchbinder | 604/96 |
| 4,969,875 | 11/1990 | Ichikawa | 604/164 |
| 4,986,814 | 1/1991 | Burney et al. | 604/281 |
| 4,997,419 | 3/1991 | Lakatos et al. | 604/164 |
| 5,026,350 | 6/1991 | Tanaka | 604/164 |
| 5,037,430 | 8/1991 | Hasson | 606/119 |

OTHER PUBLICATIONS

Mallinckrodt, Inc. Flexguide Intubation Guide-Cat, #85867 Instructions.
Weck Company-Model Nos. 153510 and 153530 Catalog page.

Primary Examiner—Stephen C. Pellegrino
Assistant Examiner—Glenn Dawson
Attorney, Agent, or Firm—Wood, Phillips, VanSanten, Hoffman & Ertel

[57] ABSTRACT

A guide structure for facilitating the performance of internal surgery. The guide structure has a guide tube with proximal and distal ends. The guide tube defines an internal, through working passageway. Structure is provided for bending the distal end of the guide tube within a range of bend angles from a location remote from the distal end of the guide tube and for releasably holding the distal end of the guide tube at a preselected bend angle within the range of bend angles.

24 Claims, 3 Drawing Sheets

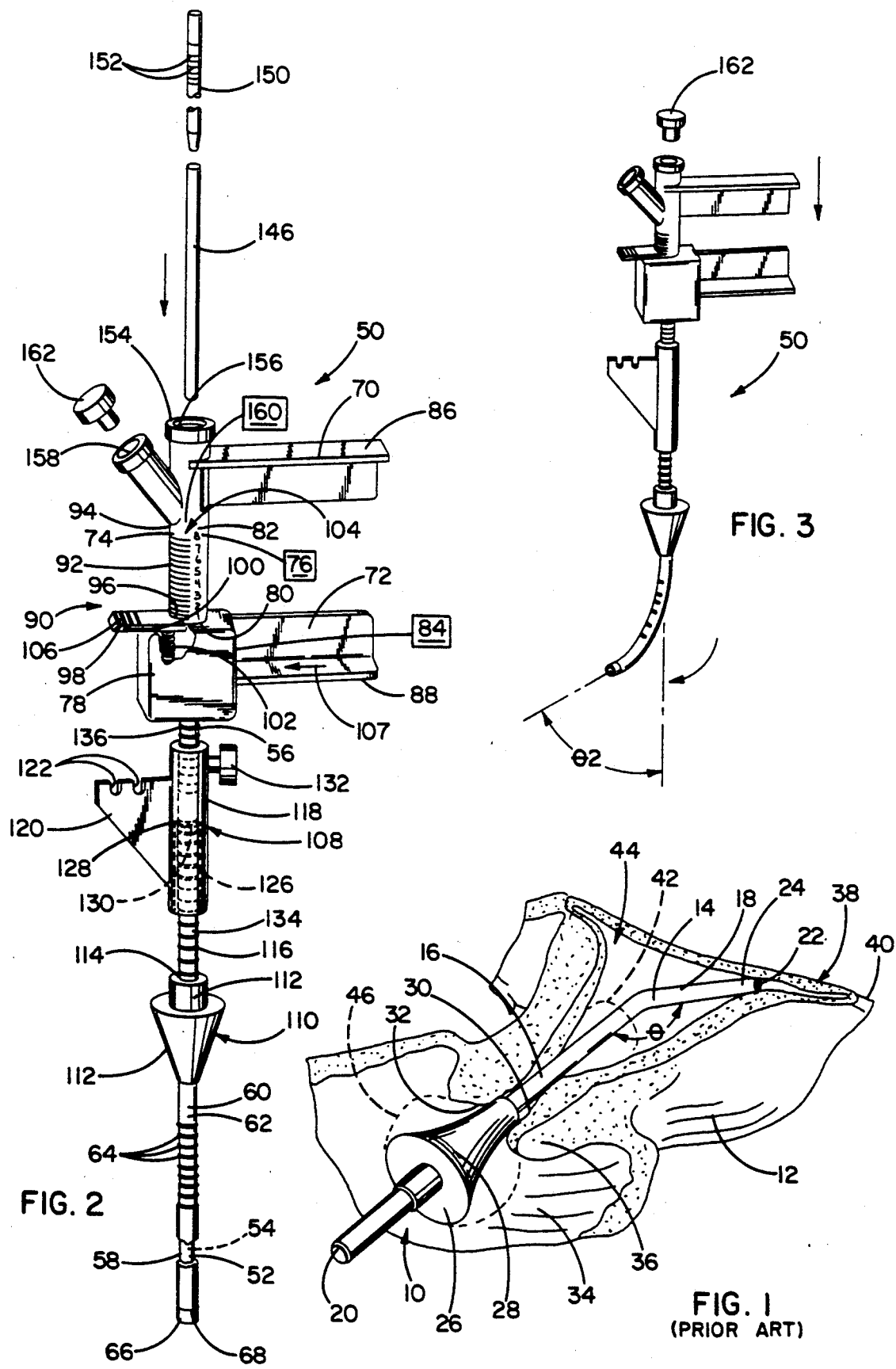

GUIDE FOR FACILITATING THE PERFORMANCE OF INTERNAL SURGERY

BACKGROUND OF THE INVENTION

1. Field of the Invention

This invention relates to instruments for performing internal surgical procedures and, more particularly, to a guide for facilitating the controlled direction of a surgical instrument into a body cavity.

2. Background Art

Recently it has become possible to access and cannulate the fallopian tubes through the cervix, uterus and utero-tubal junction using a vaginal approach. This is becoming increasingly popular because the procedures are performed in outpatient settings without surgical incisions. Some of the cannulation procedures utilizing this approach include: (1) opening blocked tubes with a small catheter carrying a balloon or with a guide wire or a combination thereof (balloon tuboplasty); (2) injecting dye selectively into the fallopian tubes for x-ray visualization (selective salpingography); (3) injection of semen into the tube (intratubal insemination); (4) deposition of embryos or gamete mixtures into the tube (intratubal embryo transfer); and (5) direct visualization of the tubal lumen with small fibrooptic flexible telescopes.

Tubal cannulation through the distal fimbrial end continues to be a popular procedure performed at laparoscopy. Existing devices utilize the concept of catheters with preformed curves to access the tubal ostia. These catheters may be constructed from bent, relatively heavy gauge metal tubing. Alternatively, the preformed curve may be maintained in flexible tubing with metallic guide wire and/or memory of the tubing, made from plastic, or the like.

To accommodate anatomic variations in the uterus, devices are made with different preformed curves. Current devices suffer from the following common limitations. (1) It is often difficult to traverse the cervical canal and gain entrance into the uterine cavity using devices with a stiffened preformed curve. The curved device may not easily pass through the straight cervix. (2) Once inside the uterine cavity, it is not easy to position the device to one side or another because the uterine cavity is shaped like a flat envelope that does not possess a significant depth dimension. The curved device can get distorted and cause the patient pain in the process of turning because there is no room for the curved portion to turn in the flat cavity. Further, it is difficult to maintain the line of the bent free end in the device in a desired orientation. Rotation of the device even a small amount about its length may completely misalign the working free end of the device. (3) Although it is useful to accommodate the individual angle variations of the uterotubal junction with devices having different curves, that entails using more than one device to accomplish a good fit. The introduction of several devices into the uterus makes the procedure less economical, more painful, and subjects the patient to increased risk of infection and bleeding. (4) The absence of uterine measurements at the time of the procedure may cause uterine injury if the device is inserted deeper than indicated by the length of the uterus or result in malposition of the catheter if the device is withdrawn excessively. (5) The absence of a stable orientation and position of the device relative to the uterus may cause the device to become misoriented or displaced during manual manipulation of a small inner catheter directed therethrough. It is common to remove a wire, or the like, that guides the device into place after the device is fully inserted. This may result in deformation and misalignment of the device.

It is also known to both seal the cervix opening and fix the device relative to the cervix by using inflatable membranes. The inflation of a membrane in the uterus can cause pain and cramping. Further the membrane can cause uterine spasms and distortion of the uterus that may inhibit the effective performance of various procedures.

SUMMARY OF THE INVENTION

The present invention contemplates a guide structure for facilitating the performance of internal surgery. The guide structure has a guide tube with proximal and distal ends. The guide tube defines an internal, through working passageway. Structure is provided for bending the distal end of the guide tube within a range of bend angles from a location remote from the distal end of the guide tube and for releasably holding the distal end of the guide tube at a preselected bend angle within the range of bend angles.

The present invention has particular utility in the uterine cavity as to access the fallopian tubes for purposes of intratubal insemination, etc. With the inventive structure, the guide tube can be conveniently directed through the cervical canal in a substantially straight orientation after which the distal end of the guide tube can be bent at a preselected angle to define a guideway into the fallopian tube. This obviates the need for having to force a pre-bent guide tube through the cervical canal which may cause discomfort and possible injury to the patient. Because the bend angle can be consistently selected, the advantages of a prebent, rigid guide tube are realized.

To effect bending of the guide tube, a second tube, with at least one cutout therein, surrounds the guide tube. The guide and second tubes are connected to each other so that relative lengthwise shifting effects bending of the guide and second tubes.

To conveniently set, hold and release the bend angle at the distal end of the guide tube, a ratchet mechanism is provided. Preferably closely spaced ratchet teeth are provided to allow fine adjustment. A release tab is associated with the ratchet mechanism to allow the guide tube to be relaxed to a normal, straight position.

As a further convenience to the surgeon, the guide and second tubes are relatively repositioned through first and second radially extending arms, connected one each to the guide and second tubes. A surgeon can grasp the first and second arms and, by movement of the first and second arms towards and away from each other, effect bending of the distal end of the guide tube.

Preferably, an outer sleeve surrounds the guide sleeve and is movable lengthwise relative to the guide sleeve. A sealing member, with a conical sealing surface, is also provided on the guide tube to be movable lengthwise relative thereto. Locking structure is provided to fix the position of the sleeve relative to the guide tube. The outer sleeve and sealing member are normally biased away from each other, as by a coil spring. The outer sleeve also has a structure for facilitating securing of the outer sleeve relative to a tissue through which the guide tube is extended.

With the above structure, the guide tube can be secured to a tissue through which the guide structure extends, as by the use of a tenaculum. A radially projecting arm has preferably a plurality of notches to accept the tenaculum to accommodate different body sizes. The tenaculum biasably urges the sealing member into the opening in the tissue through which the guide structure extends.

Preferably, the guide tube has a first opening/port at its proximal end with a sealing cap that can be selectively placed to expose and seal the guide tube opening.

To facilitate introduction of fluid into the guide tube passageway, a second port, separate from the guide tube opening/port, is provided in communication with the guide tube passageway. A sealing cap is useable to selectively close and expose the second port.

To facilitate direction of the guide tube into a cavity a predetermined extent and the setting of a preselected bend angle for the distal end of the guide tube, scales are provided. The guide tube preferably has a graduated scale through which the amount of extension of the guide tube through the outer sleeve can be visually observed. Another scale is provided on the ratchet mechanism to give a visual indication of the bend angle for the distal end of the guide tube.

BRIEF DESCRIPTION OF THE DRAWINGS

FIG. 1 is a perspective view of a prior art surgical guide structure operatively associated with a uterus;

FIG. 2 is a perspective view of a preferred form of surgical guide structure according to the present invention and showing a guide tube thereon in a straight orientation;

FIG. 3 is a view as in FIG. 2 with the guide tube set at a predetermined bend angle;

DETAILED DESCRIPTION OF THE DRAWINGS

Figure 4:
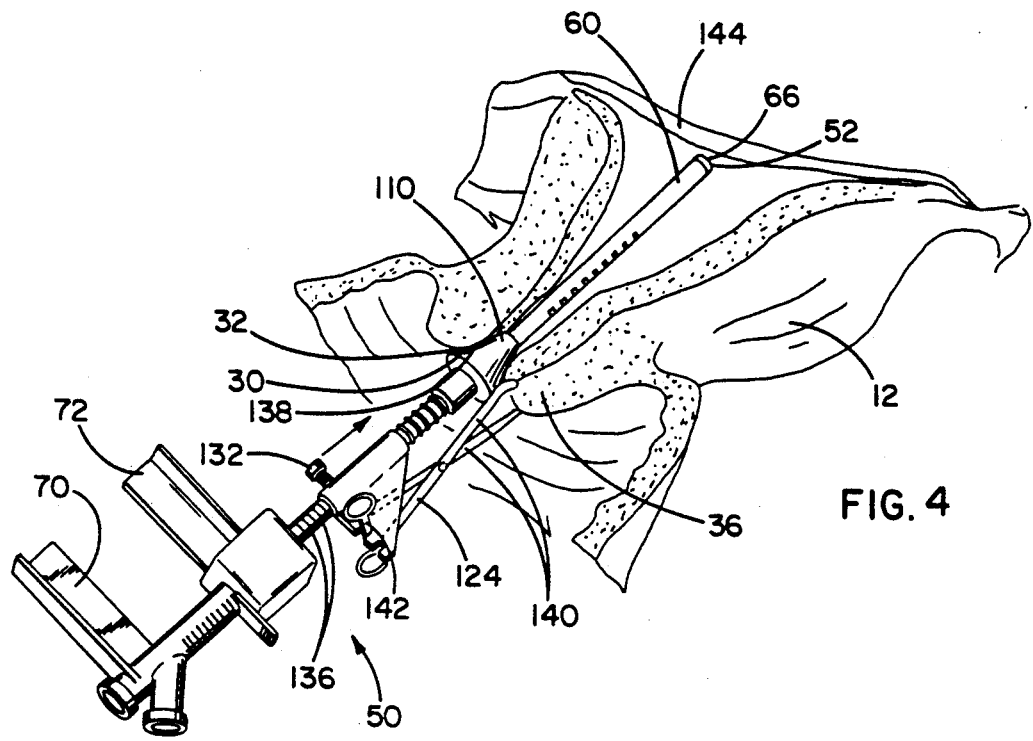
FIG. 4 is a perspective view of the inventive guide structure placed operatively within a uterus in its FIG. 2 orientation.

In FIG. 1, a prior art guide structure for facilitating the performance of intrauterine surgery is shown at 10 in operative association with a uterus 12. The guide structure 10 consists of a metal guide tube 14 having a straight body 16 and an offset end 18 making an angle $\theta$ with the body 16. The guide tube 14 defines an internal passageway 20 for guiding a surgical instrument from a point externally of the uterus 12, through the uterus 12, and angularly outwardly through an opening 22 at the distal end 24 of the guide tube 14.

The guide tube 14 has a surrounding sealing member 26 which is movable lengthwise relative to the guide tube body 16. The sealing member 26 has a tapered sealing surface 28 which is directed into the cervical canal 30 to seal the cervical opening 32.

To place the guide structure 10 in its operative position, the offset guide tube end 18 must be forced through the cervical canal 30. This requires that the surgeon tilt the entire guide structure 10. Even by tilting the guide structure 10 to the maximum extent permitted within the vagina 34, the cervix 36 must be stretched. This may cause pain and/or injury to the patient. Once the offset end 18 is directed through the cervical canal 30, the offset end 18 may hang up on the uterus 12 as it is directed into its operative position of FIG. 1, in which the length of the offset end 18 is aligned at the uterotubal junction 38 to facilitate direction of an instrument into the fallopian tube 40.

Once the guide tube 14 is in its operative position, a bladder 42 can be inflated to maintain the sealing member 26 securely in the cervical opening 32 and thereby seal the uterine cavity 44. The bladder 42 may cause discomfort to the patient and may possibly induce spasms that hamper the performance of the surgical procedure.

In FIG. 1, an optional bladder 46 is shown externally of the uterine cavity 44 to cooperate with the bladder 42 to maintain the guide structure 10 in place and the uterine cavity 44 sealed. The bladder 46 may be used as an alternative to the more rigid sealing member 26 in FIG. 1.

In FIGS. 2-5, a first form of a guide structure for surgical instruments, according to the present invention, is shown at 50. The guide structure 50 consists of a flexible guide tube 52, made preferably from plastic and defining an internal working passageway 54. The guide tube 52 has proximal and distal ends 56, 58, respectively, with the distal end 58 being advanceable through an opening in tissue surrounding a cavity in which a surgical procedure is to be performed.

The guide tube 52 is surrounded by a second flexible/plastic tube 60 having a peripheral wall 62 with a plurality of axially spaced slits 64 therethrough. The free end 66 of the guide tube 52 is connected to the free end 68 of the second tube 60. By attempting to draw the second tube 60 upwardly/axially relative to the guide tube 52, the second tube is caused to collapse/bend, as readily permitted by the slits 64, as shown in FIG. 3. The bend angle for the distal end 58 of the guide tube 52 is identified as $\theta 2$ in FIG. 3 and preferable ranges from 0°-90°.

Relative lengthwise shifting between the guide tube 52 and second tube 60 is accomplished through first and second arms 70, 72, respectively. The first arm 70 projects radially from a cylindrical sleeve 74 at the proximal end of the guide structure 50. The arm 70 has an L-shaped cross section to give it rigidity. The sleeve 74 is fixedly secured to the guide tube 52 by a means shown schematically at 76. The construction of a suitable securing means 76 is within the knowledge of one skilled in the art.

A squared housing 78 has a guide opening 80 therethrough and supports the second arm 72 in cantilever fashion. The body 82 of the sleeve 74 is movable within the opening 80 to permit guided movement of the arms 70, 72 towards and away from each other. The housing 78 is fixedly secured by a means 84, also of a type well known to those skilled in the art, to the second tube 60. The second arm 72 has an L-shaped cross section as the first arm 70. The arms 70, 72 are arranged so that oppositely facing flat surfaces 86, 88 on the arms 70, 72, respectively, can be readily grasped by the user who can then squeeze the arms 70, 72 in one hand to effect movement of the arms 70, 72, one towards the other. As this occurs, the guide and second tubes 52, 60 shift and resultingly the distal end 58 of the guide tube 52 is progressingly bent.

To facilitate setting and holding of the desired bend angle 82 for the distal end 58 of the guide 52, a ratchet mechanism is provided at 90. The ratchet mechanism 90 consists of a plurality of axially spaced teeth 92 on the outer surface 94 of the sleeve 74. The teeth 92 cooperate with a curved edge 96 on a ratchet tab 98 that is pivotable about a pin 100 to selectively a) place the edge 96 in engagement with the teeth 92 and b) separate the edge 96 from the teeth 92.

The tab 98 is normally biased by a spring 102 to a neutral position in which the edge 96 resides between adjacent teeth 92. As the sleeve 74 moves downwardly into the guide opening 80, the edge 96 moves in and out between adjacent teeth 92 against the bias of the spring 102. The cooperating tab 98 and teeth 92 thus maintain the guide and second tubes 52, 60 in a desired relationship to produce and maintain a range of bend angles for the distal end 58 of the guide tube 52. The teeth 92 serve as graduations which are numbered as at 104 to give a visual indication of the relative positions of the guide and second tubes 52, 60 and allow consistent re-setting of the bend angle for the guide tube 52.

By pressing down on a ribbed surface 106 of the tab 98, the tab 98 pivots about the pin 100 to disengage the edge 96 from the teeth 92 to allow unimpeded relative movement between the guide and second tubes 52, 60.

Preferably, the arms 70, 72 have their lengths generally aligned to be parallel with the path traced by the distal end 58 of the guide tube 52 as it is repositioned. Consequently, the operator of the guide structure 50 can readily visually determine the direction of bending and amount of bend angle for the guide tube 52 from outside of the cavity in which the surgery is performed. An indicating arrow 107 (FIG. 1) on the arm 72 gives a further visual indication of the bending direction of the guide tube 52.

To facilitate mounting of the guide tube 52 with respect to a tissue through which the guide structure is extended, an outer sleeve 108 and sealing member 110 are provided on the second tube 60 and are each slidable lengthwise therealong. The sealing member 110 has a conical surface 112 which seals an opening through which the guide structure 50 extends, as described below. The sealing member 110 has a cylindrical extension 112 defining a receptive socket 114 for one end of a spring 116 that is utilized to bias the sealing member 110 away from the outer sleeve 108.

The outer sleeve 108 has a cylindrical body 118 with a radially projecting arm 120 which facilitates securing of the guide structure 50 with respect to tissue through which the guide structure 50 extends. The arm 120 has radially spaced notches 122 for mounting a tenaculum 124 (FIG. 4), as described in detail below. The body 118 has a stepped bore 126 therethrough defining a shoulder 128 for the spring end 130. A locking screw 132 fixes the body 118 in desired position along the second tube 60.

The outer surface 134 of the second tube 60 has graduations 136 thereon to give the user a visual indication of the relative positions of the guide and second tubes 50, 60, respectively. This alerts the user to the amount of extension of the distal tube end 58 into a cavity.

The application of the guide structure 50 will now be described with respect to FIGS. 4 and 5, which show the guide structure 50 operatively associated with a uterus 12. With the guide tube 52 in its straight position of FIG. 2, it can be conveniently directed through the cervical canal 30 with minimal resistance. The sealing member 110 is then pressed into the cervical opening 32 in sealing engagement with the surrounding cervical wall 138. The working end of the tenaculum 124, which is of a conventional construction, has jaws 140 which cooperatively grip the cervix 36. The opposite end of the tenaculum 124 has a holding bar 142 which is then placed in one of the notches 122 on the securing arm 120 on the outer sleeve 108. This results in the sleeve 108 being held in a substantially fixed position relative to the cervix 36 and causes the spring 116 to thereby exert an inward bias on the sealing member 110 which thereby effects a positive seal at the cervical opening 32. At the same time this arrangement straightens out any degree of ante- or retroversion which would occur in the absence of the tenaculum 124.

The guide and second tubes 52, 60 are then pressed into the uterus until the free end 66 of the guide tube 52 encounters the top of the fundus 144. The guide and second tubes 52, 60 are then backed out from 0.5 to 1.5 centimeters to optimize the position of the guide tube 52. This position for the guide and second tubes 52, 60 is then maintained by the locking screw 132.

To facilitate direction of the guide tube 52 into place without buckling, an optional stiffening rod 146 (FIG. 2) can initially be extended through the guide tube 52. Once the guide tube 52 is in place, the stiffening rod 146 can be removed to open the passageway 54 defined by the guide tube 52. The amount of extension of the guide tube 52 into the uterus 12 can be readily ascertained by observing the graduations 136 on the second tube 60.

Figure 5:
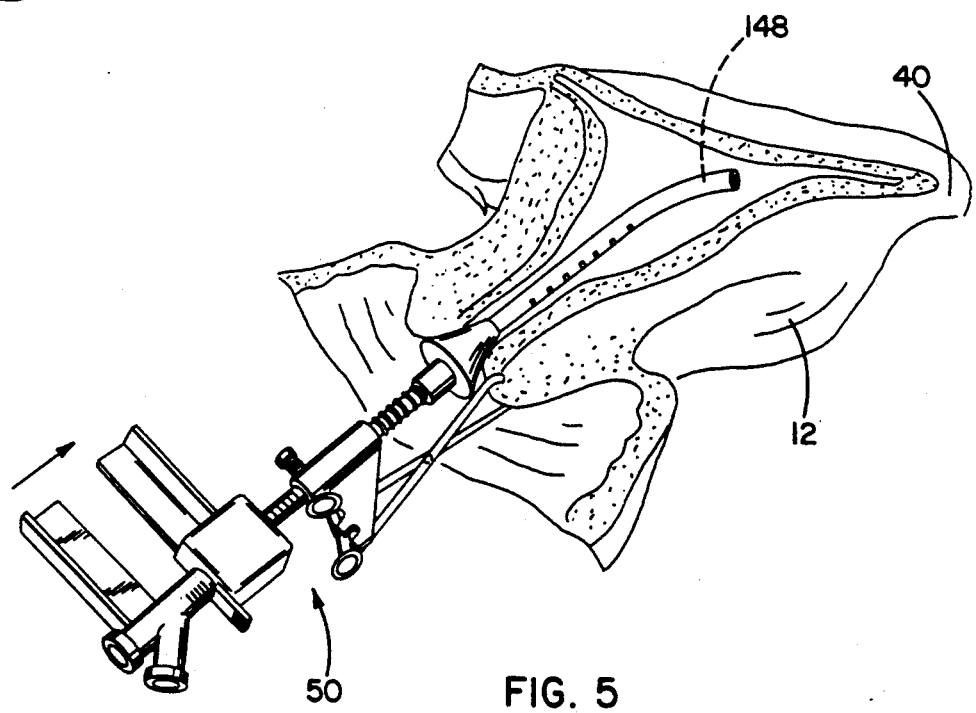
FIG. 5 is a view as in FIG. 4 with the guide tube bent to facilitate direction of an instrument into the fallopian tube.

The user can then urge the arms 70, 72 towards each other to produce the desired bend angle, as shown in FIG. 5. The ratchet mechanism 90 maintains the desired bend angle for the distal end 58 of the guide tube 52.

The teeth 92 are preferably spaced sufficiently close together that fine adjustments to the bend angle can be made. The preferred bend angle in FIG. 5 aligns the line of the bent portion 148 at the distal end 58 of the guide tube 52 with the fallopian tube 40 to facilitate passage of an instrument thereinto. The invention does contemplate various other structures for setting and maintaining the bend angle for the guide tube 52.

A measuring tube 150 can be directed through the guide structure 50 in its operative position of FIG. 5. The tube 150 has graduations 152 thereon to give the user a visual indication of the distance from the top edge 154 of the guide structure 50 to the free end 66 of the guide tube 52. By withdrawing the measuring tube 150, the user can then determine the exact length of instrument required to be directed through the guide structure 50 into the fallopian tube 40.

Once the procedure is completed, the tenaculum 124 can be released to allow withdrawal of the entire guide structure 50.

Another aspect of the invention is the provision of separate ports 156, 158 in communication with the tube passageway 54. The primary port 156 defines the entryway for the surgical instruments that are employed. The secondary port 158 provides means for injecting a fluid into a cavity, which fluid may be saline or a dye, depending upon the procedure. An optional one-way valve 160 can be used to allow introduction of instruments and fluid while obstructing return flow of fluid through the passageway 54. A sealing cap 162 can be removably placed in each of the ports 156, 158 to effect sealing thereof.

Figure 6:
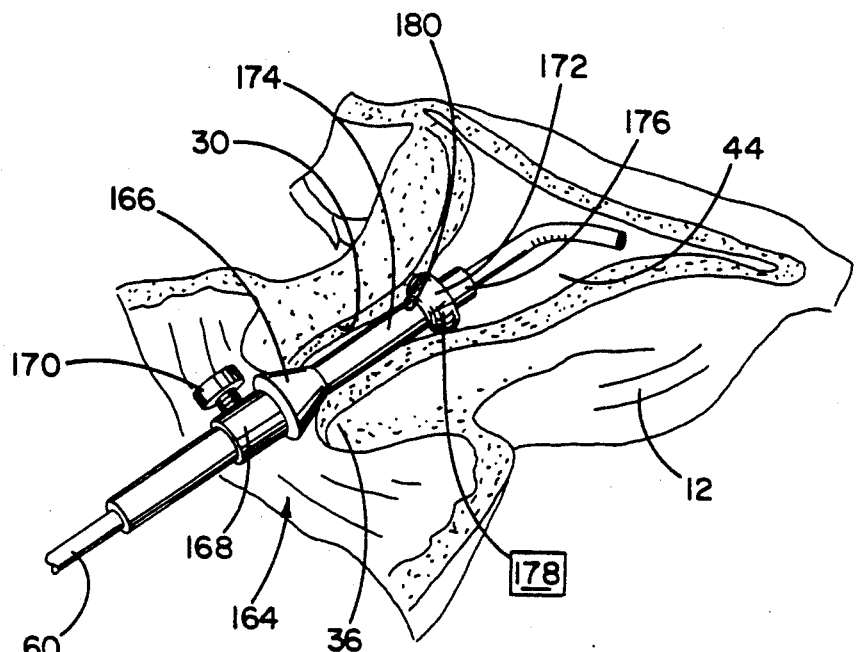
FIG. 6 is a modified form of guide structure for a surgical instrument according to the present invention and operatively positioned within a uterus.

If internal, optical monitoring of a procedure is carried out, a modified form of the guide structure according to the present invention, as shown at 164 in FIG. 6, can be employed. The guide structure 164 employs a conical sealing member 166 with a sleeve extension 168 and locking nut 170 thereon and a spaced, inflatable bladder 172, shown in FIG. 6 in its inflated state. The sealing member 166 and bladder 172 are incorporated into a guide tube 174 that is directed through the cervical canal 30. The bladder 172 is provided at the distal end 176 of the guide tube 174. The sealing member 166 and associated sleeve 168 are slidable towards and away from the bladder 172 on the guide tube 174.

Once the guide tube 174 is inserted through the cervical canal 30, the bladder 172 can be inflated through a supply 178 of liquid or gas to define a shoulder 180 that prevents withdrawal of the bladder from the uterine cavity 144. The sleeve extension 168 and sealing member 166 can then be slid towards the bladder 172 so that the cervix 36 is held captive between the bladder 172 and sealing member 166.

The second tube 60 and guide tube 52 can then be directed as a unit through the tube 174 into operative position as in the previously described embodiment.

If the procedure is monitored optically, it is unnecessary to provide the scale to determine the exact bend angle for the guide tube 52 as well as the amount of extension into the uterus 12. The surgeon can visually monitor the position and angle of the guide tube 42.

Figure 7:
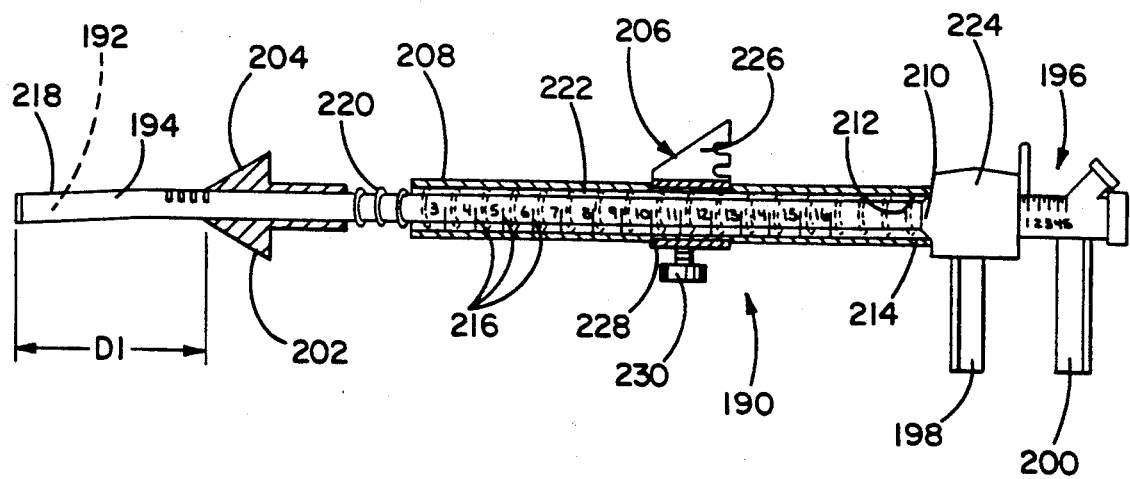
FIG. 7 is a side elevation view of a further modified form of surgical guide structure according to the present invention.

A modified form of surgical guide structure, according to the present invention, is shown at 190 in FIG. 7. The guide structure 190 is similar to that 10 shown in FIGS. 1-5 and includes a guide tube 192, a surrounding, slotted, second tube 194, a ratchet mechanism at 196 operable by radially projecting arms 198, 200, a sealing member 202 with a conical sealing surface 204, and a mechanism 206 to facilitate maintaining of the guide structure 190 in its operative position.

An outer sleeve 208 loosely surrounds the second tube 194 and is maintained in coaxial relationship therewith by a tapered locating boss 210, which fits in an opening 212 at a proximal end 214 of the outer sleeve 208. The outer sleeve 208 is preferably clear to allow viewing of graduations 216 on the second tube 194 to give an indication of the amount of penetration of the distal end 218 of the second tube 194 within the cavity within which the operation is being performed.

A single coil spring 220 surrounds the second tube 194 and resides partially within a radial space 222 between the second tube 194 and outer sleeve 208. The spring 220 exerts a bias between a housing 224 on the ratchet mechanism 196 and the sealing member 202.

The mechanism 206 has an arm 226 projecting radially outwardly of the structure 190 to support a tenaculum (not shown). The mechanism 206 has an integral sleeve 228 which guides axial movement relative to the underlying sleeve 208. A set screw 230 holds the sleeve 228 in a desired position relative to the outer sleeve 208. By tightening the set screw 230, the sleeve 208 is slightly collapsed in a radial direction so that the relative positions of the outer sleeve 208 and sleeve 228 are positively maintained.

It should be understood that while the inventive structure is particularly useful as an intrauterine guide, it is useful in any environment wherein an instrument is passed through a tissue to perform a surgical procedure within a cavity bounded by the tissue.

The foregoing disclosure of specific embodiments is intended to be illustrative of the broad concepts comprehended by the invention.

I claim:

1. An assembly for performing internal surgery, said assembly comprising:
   a guide tube having a proximal end and an open distal end and defining an internal through passageway for a surgical instrument;
   means for bending the distal end of the guide tube within a range of bend angles from a location remote from the distal end of the guide tube;
   means for releasably holding the distal guide tube end at a preselected bend angle within the range of bend angles; and
   an elongate surgical instrument for passage through the guide tube passageway to outward of the open distal end of the guide tube,
   wherein said holding means comprises ratchet means,
   wherein the bending means includes a second tube, each said guide and second tubes having an axis and residing one at least partially within the other.

2. The surgical instrument according to claim 1 wherein the guide tube has a first opening/port at its proximal end and means are provided for selectively sealing and exposing the opening at the proximal end of the guide tube.

3. A guide structure for facilitating the performance of internal surgery, said guide structure comprising:
   a guide tube having proximal and distal ends and defining an internal through passageway;
   means for bending the distal end of the guide tube within a range of bend angles from a location remote from the distal end of the guide tube; and
   means for releasably holding and locking the distal guide tube end at a preselected bend angle within the range of bend angles,
   wherein the bending means includes a second tube, each said guide and second tubes having an axis and residing one at least partially within the other, said bending means including cooperating means on the guide and second tubes for increasing the bend angle of the distal end of the guide tube as the second tube is moved in a first axial direction relative to the guide tube and for decreasing the bend angle of the distal end of the guide tube as the second tube is moved in a second axial direction relative to the guide tube.

4. A guide structure for facilitating the performance of internal surgery, said guide structure comprising:
   a guide tube having a proximal and distal ends and defining an internal through passageway;
   means for bending the distal end of the guide tube within a range of bend angles from a location remote from the distal end of the guide tube; and
   means for releasably holding the distal guide tube end at a preselected bend angle within the range of bend angles,
   wherein the bending means includes a second tube, each said guide and second tubes having an axis and residing one at least partially within the other, said bending means including cooperating means on the guide and second tubes for increasing the bend angle of the distal end of the guide tube as the second tube is moved in a first axial direction relative to the guide tube and for decreasing the bend angle of the distal end of the guide tube as the second tube is moved in a second axial direction relative to the guide tube wherein the guide tube resides within the second tube and the second tube has a peripheral wall with at least one cutout therein to facilitate flexing thereof to alter the bend angle of the distal end of the guide tube.

5. A guide structure for facilitating the performance of internal surgery, said guide structure comprising:

a guide tube having proximal and distal ends and defining an internal through passageway;

means for bending the distal end of the guide tube within a range of bend angles from a location remote from the distal end of the guide tube; and means for releasably holding the distal guide tube end at a preselected bend angle within the range of bend angles, wherein the bending means includes a second tube, each said guide and second tubes having an axis and residing one at least partially within the other, said bending means including cooperating means on the guide and second tubes for increasing the bend angle of the distal end of the guide tube as the second tube is moved in a first axial direction relative to the guide tube and for decreasing the bend angle of the distal end of the guide tube as the second tube is moved in a second axial direction relative to the guide tube, wherein the holding means comprises a releasable ratchet mechanism.

6. The guide structure according to claim 5 wherein the bending means includes first and second arms extending radially with respect to the axes of the guide and second tubes, said first and second arms being connected one each to the guide and second tubes, said bending means being operable by grasping the first and second arms and moving the first and second arms axially, selectively towards and away from each other.

7. The guide structure according to claim 5 wherein the ratchet mechanism includes a pivotable release tab.

8. A guide structure for facilitating the performance of internal surgery, said guide structure comprising:

a guide tube having proximal and distal ends and defining an internal through passageway;

means for bending the distal end of the guide tube within a range of bend angles from a location remote the distal end of the guide tube; and means for releasably holding the distal guide tube end at a preselected bend angle within the range of bend angles, said guide structure further including an outer sleeve surrounding the guide tube and movable lengthwise relative to the guide tube, a sealing member with a conical surface on at least one of the guide tube and outer sleeve to be sealingly engaged within a tissue surrounding an opening through which the guide tube is extended, and means for normally biasing the sealing member away from the outer sleeve.

9. The guide structure according to claim 8 wherein the outer sleeve includes means for facilitating securing of the outer sleeve relative to a tissue through which the guide tube is extended.

10. The guide structure according to claim 9 wherein the securing means comprises a radially extending arm on the outer sleeve with at least one notch therein for accommodating a tenaculum that can be used to connect the outer sleeve to a tissue through which the guide tube is extended.

11. A guide structure for facilitating the performance of internal surgery, said guide structure comprising:

a guide tube having proximal and distal ends and defining an internal through passageway;

means for bending the distal end of the guide tube within a range of bend angles from a location remote from the distal end of the guide tube; and means for releasably holding and locking the distal guide tube end in a plurality of preselected bend angles within the range of bend angles said holding and locking means further comprising incremental adjusting means for locking said guide tube end at each of said plurality of preselected bend angles, wherein the guide tube has a first opening/port at its proximal end and means are provided for selectively sealing and exposing the opening at the proximal end of the guide tube, said guide structure further including a second opening/port at the proximal end of the guide tube in communication with the internal passageway defined by the guide tube.

12. A guide structure for facilitating the performance of internal surgery, said guide structure comprising:

a guide tube having proximal and distal ends and defining an internal through passageway, said guide tube in a normal relaxed state having a straight configuration;

means for bending the distal end of the guide tube within a range of bend angles from a location remote from the distal end of the guide tube; and means for releasably holding the distal guide tube end at a preselected bend angle within the range of bend angles, wherein the guide tube has a first opening/port at its proximal end and means are provided for selectively sealing and exposing the opening at the proximal end of the guide tube, said guide structure further including scale means on the guide structure for giving a visual indication of the bend angle of the distal end of the guide tube at a location remote from the distal end of the guide tube.

13. A guide structure for facilitating the performance of internal surgery, said guide structure comprising:

a guide tube having proximal and distal ends and defining an internal through passageway;

means for bending the distal end of the guide tube within a range of bend angles from a location remote from the distal end of the guide tube;

means for releasably holding the distal guide tube end at a preselected bend angle within the range of bend angles, said guide structure further including an outer sleeve surrounding the guide tube and movable lengthwise relative to the guide tube, a sealing member with a conical surface on at least one of the guide tube and outer sleeve to be sealingly engaged within a tissue surrounding an opening through which the guide tube is extended, and means for normally biasing the sealing member away from the outer sleeve; and scale means on the guide structure for giving a visual indication of the relative positions of the outer sleeve and guide tube.

14. A guide structure for facilitating the performance of internal surgery, said guide structure comprising:

a guide tube having proximal and distal ends and defining an internal through passageway;

means for bending the distal end of the guide tube within a range of bend angles from a location remote from the distal end of the guide tube;

means for releasably holding the distal guide tube end at a preselected bend angle within the range of bend angles;

said guide structure further including an outer sleeve surrounding the guide tube and movable lengthwise relative to the guide tube, a sealing member with a conical surface on at least one of the guide tube and outer sleeve to be sealingly engaged within a tissue surrounding an opening through which the guide tube is extended, and means for normally biasing the sealing member away from the outer sleeve; and cooperating means on the outer sleeve and the guide tube for releasably fixing the relative axial positions of the outer sleeve and the guide tube.

15. A guide structure for facilitating the performance of internal surgery, said guide structure comprising:

a guide tube having a proximal end and a distal end with an opening and defining an internal through passageway;

means for bending the distal end of the guide tube within a range of bend angles from a location remote from the distal end of the guide tube, said bending means including a second tube and cooperating means on the guide and second tubes for varying the bend angle of the distal end of the guide tube by moving the guide and second tubes one within the other lengthwise relative to each other;

means on at least one of the guide and second tubes for sealing an opening through which the guide structure is extended;

means remote from the distal end of the guide tube for giving a visual indication of the direction of bending of the distal end of the guide tube to allow the user of the guide structure to ascertain the location of the opening at the distal end of the guide tube and the direction that an instrument extended through the guide tube passageway and out the guide tube opening will move in; and means for releasably locking the distal end of the guide tube at a preselected bend angle.

16. The guide structure according to claim 15 including means for holding a plurality of preselected bend angles for the distal end of the guide tube in the range of bend angles.

17. A guide structure for facilitating the performance of internal surgery, said guide structure comprising:

a guide tube having a proximal end and a distal end with an opening and defining an internal through passageway;

means for bending the distal end of the guide tube within a range of bend angles from a location remote from the distal end of the guide tube, said bending means including a second tube and cooperating means on the guide and second tubes for varying the bend angle of the distal end of the guide tube by moving the guide and second tubes on within the other lengthwise relative to each other;

means on at least one of the guide and second tubes for sealing an opening through which the guide structure is extended;

means remote from the distal end of the guide tube for giving a visual indication of the direction of bending of the distal end of the guide tube to allow the user of the guide structure to ascertain the location of the opening at the distal end of the guide tube and the direction that an instrument extended through the guide tube passageway and out the guide tube opening will move in; and means for holding a plurality of preselected bend angles for the distal end of the guide tube in the range of bend angles, wherein the means for holding a plurality of preselected bend angles comprises a ratchet mechanism.

18. A guide structure for facilitating the performance of internal surgery, said guide structure comprising:

a guide tube having a proximal end and a distal end with an opening and defining an internal through passageway;

means for bending the distal end of the guide tube within a range of bend angles from a location remote from the distal end of the guide tube, said bending means including a second tube and cooperating means on the guide and second tubes for varying the bend angle of the distal end of the guide tube by moving the guide and second tubes one within the other lengthwise relative to each other;

means on at least one of the guide and second tubes for sealing an opening through which the guide structure is extended;

means remote from the distal end of the guide tube for giving a visual indication of the direction of bending of the distal end of the guide tube to allow the user of the guide structure to ascertain the location of the opening at the distal end of the guide tube and the direction that an instrument extended through the guide tube passageway and out the guide tube opening will move in; and graduated scale means for giving a visual indication of the relative positions of the sealing means and the guide tube.

19. A guide structure for facilitating the performance of internal surgery, said guide structure comprising:

a guide tube having a proximal end and a distal end within an opening and defining an internal through passageway;

means for bending the distal end of the guide tube within a range of bend angles from a location remote from the distal end of the guide tube, said bending means including a second tube and cooperating means on the guide and second tubes for varying the bend angle of the distal end of the guide tube by moving the guide and second tubes one within the other lengthwise relative to each other;

means on at least one of the guide and second tubes for sealing an opening through which the guide structure is extended; and means remote from the distal end of the guide tube for giving a visual indication of the direction of bending of the distal end of the guide tube to allow the user of the guide structure to ascertain the location of the opening at the distal end of the guide tube and the direction that an instrument extended through the guide tube passageway and out the guide tube opening will move, wherein the bending means includes first and second arms extending transverse to the length of the guide and second tubes and means for connecting the first and second arms, one each of the guide and second tubes, to thereby facilitate bending of the distal end of the guide tube by relative movement of the guide and second tubes by movement of the first and second arms towards and away from each other.

20. A guide structure for facilitating the performance of internal surgery, said guide structure comprising:
 a guide tube having proximal and distal ends with an opening at the distal end thereof and defining a through passageway in communication with the distal end opening;
 means for bending the distal end of the guide tube within a range of bend angles from a location remote from the distal end of the guide tube,
 said bending means including a second tube surrounding the guide tube and having a plurality of cutouts therethrough and means for connecting the guide and second tubes together so that relative lengthwise movement between the guide and second tubes effects bending of the distal end of the guide tube,
 said bending means further including first and second arms extending transversely with respect to the length of the guide and second tubes and means for connecting the first and second arms, one each to the guide and second tubes, to allow relative lengthwise movement to be effected between the guide and second tubes by selective movement of the first and second arms towards and away from each other;
 an outer sleeve surrounding the guide and second tubes and slidable lengthwise relative thereto;
 means for fixing the position of the outer sleeve relative to at least one of the guide and second tubes;
 a sealing member connected to at least one of the guide tube, outer sleeve and second tube and having a conical sealing surface to be pressed against tissue surrounding an opening through which the guide structure is extended;
 means for normally biasing the outer sleeve and sealing member away from each other;
 mean on the outer sleeve for connecting an end of a tenaculum to hold the outer sleeve relative to a tissue through which the guide tube extends; and
 means for setting and releasably holding the proximal end of the guide tube at a preselected bend angle.

21. The guide structure according to claim 20 including graduated scale means for giving a visual indication of the relative position of one of the guide and second tubes and one of the outer sleeve and sealing member.

22. The guide structure according to claim 20 including graduated scale means for giving a visual indication of the relative positions of the guide and second tubes.

23. The guide structure according to claim 20 including a first port defining an entryway for an instrument at the proximal end of the guide tube and a second port, separate from the first port, defining a communication path with the guide tube passageway at the proximal end of the guide tube to externally of the guide structure.

24. The guide structure according to claim 23 including first and second means for selectively sealing and exposing the first and second ports.

* * * * *